United States Patent [19]

Vanlerberghe et al.

[11] Patent Number: 5,298,242

[45] Date of Patent: Mar. 29, 1994

[54] POLYFLUOROALKYLTHIOPOLY(ETHYLIMIDAZOLIUM) COMPOUNDS, PREPARATION PROCESS AND THEIR USE AS BIOCIDAL AGENTS

[75] Inventors: Guy Vanlerberghe, Claye-Souilly; Eric Bollens, Saint-Maurice; Claude Mahieu; Henri Sebag, both of Paris, all of France

[73] Assignee: L'Oreal, Paris, France

[21] Appl. No.: 903,023

[22] Filed: Jun. 23, 1992

[30] Foreign Application Priority Data

Jun. 24, 1991 [FR] France ................. 91 07734

[51] Int. Cl.$^5$ .............. A61K 31/74; C07D 233/00
[52] U.S. Cl. .............. 424/78.36; 548/313.7; 548/342.1; 514/399; 514/401; 424/70; 424/47
[58] Field of Search .......... 548/313.7, 342.1, 313.7, 548/78.36; 424/47, 70; 514/399, 401

[56] References Cited

U.S. PATENT DOCUMENTS

| | | | |
|---|---|---|---|
| 3,920,689 | 11/1975 | Jaeger | 548/313.7 |
| 4,210,656 | 7/1980 | Zirngibl et al. | 548/342.1 |
| 4,610,716 | 9/1986 | Sturm | 548/342.1 |

FOREIGN PATENT DOCUMENTS

| | | |
|---|---|---|
| 0162388 | 11/1985 | European Pat. Off. . |
| 0196824 | 10/1986 | European Pat. Off. . |
| 0301447 | 2/1989 | European Pat. Off. . |
| 3733471 | 4/1989 | Fed. Rep. of Germany . |
| 2275194 | 1/1976 | France . |
| 2492376 | 4/1982 | France . |

*Primary Examiner*—Thurman K. Page
*Assistant Examiner*—Peter F. Kulkosky
*Attorney, Agent, or Firm*—Jacobson, Price, Holman & Stern

[57] ABSTRACT

The invention relates to compounds of formula:

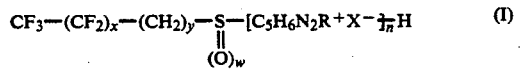

in which:
w is 0, 1 or 2;
x is between 2 and 10;
y is between 0 and 5;
R denotes a methyl, ethyl, hydroxyethyl or benzyl radical;
X$^\ominus$ denotes an inorganic or organic anion; and
n is an integer or decimal number between 1 and 15;
the [C$_5$H$_6$N$_2$R$^+$] group representing the following structures, taken as a mixture or individually:

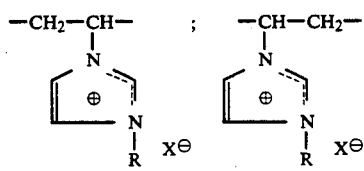

as well as their use as a biocidal agent or preservative.

6 Claims, No Drawings

POLYFLUOROALKYLTHIOPOLY(ETHYLIMIDAZOLIUM) COMPOUNDS, PREPARATION PROCESS AND THEIR USE AS BIOCIDAL AGENTS

The present invention relates to new compounds of the polyfluoroalkylthiopoly(ethylimidazolium) type, a process for their preparation and their use as biocidal agents in diverse industrial fields such as cosmetics, human and veterinary pharmacy, agriculture, paints and varnishes and papermaking.

In cosmetics, products are required which have bactericidal and/or fungicidal properties and a good tolerance with respect to the skin and hair, in particular in anti-dandruff products and in products for cleansing the skin.

In pharmacy, the use of bactericidal and/or fungicidal products is also of great interest, in particular in the treatment of diseases affecting the horny layer of the epidermis in man or in animals, such as acne, in the treatment of the mucosa or in the treatment of mycoses.

Cationic compounds of the quaternary ammonium type are commonly used as bactericidal agents in cosmetics or pharmacy. However, these compounds show tolerance problems.

Cetyltrimethylammonium bromide, better known under the name "CETAVLON", is known from the prior art.

The Applicant has discovered new compounds derived from imidazole which have a good biocidal activity, as well as a lower toxicity when compared with the known compounds. They also have good cosmetic properties with respect to the hair, the skin and the nails.

These compounds also have valuable surfactant properties.

The subject of the present invention is new cationic compounds of the imidazolium type.

Another subject of the invention is a process for the preparation of these compounds.

The invention also relates to the use of these compounds as biocidal agents in numerous fields in the chemical industry, and more particularly in cosmetics and dermopharmacy.

Further subjects will become apparent in the light of the description and the examples which follow.

The compounds according to the present invention correspond to the following formula (I):

$$CF_3-(CF_2)_x-(CH_2)_y-\underset{\underset{(O)_w}{\parallel}}{S}-[C_5H_6N_2R^+X^-]_{\overline{n}}H \quad (I)$$

in which:
  w is 0, 1 or 2;
  x is between 2 and 10;
  y is between 0 and 5;
  R denotes a methyl, ethyl, hydroxyethyl or benzyl radical;
  $X^\ominus$ denotes an inorganic or organic anion; and
  n is an integer or decimal number between 1 and 15;
  the $[C_5H_6N_2R^+]$ group representing the following structures, taken as a mixture or individually:

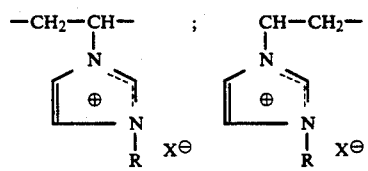

The anion $X^\ominus$ denotes halides, alkyl sulfates, alkylsulfonates or arylsulfonates.

In particular it may denote $Cl^-$, $Br^-$, $I^-$, $CH_3OSO_3^-$, $C_2H_5OSO_3^-$, $CH_3SO_3^-$ or

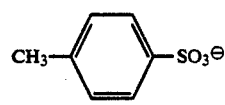

The preferred compounds according to the present invention are chosen from those of formula (I) in which w is 0.

A further subject of the invention consists of a process for the preparation of the cationic surfactants of the invention.

The compounds according to the invention may be prepared by a radical addition reaction of a mercaptan of formula:

$$CF_3-(CF_2)_x-(CH_2)_y-SH$$

in which x and y have the same meaning as indicated above, with one or more molecule(s) of 1-vinylimidazole in order to obtain a compound of the following formula (II)

$$CF_3-(CF_2)_x-(CH_2)_y-S-(C_5H_6N_2)_nH \quad (II)$$

in which the $((C_5H_6N_2))$ group represents the following structures, taken as a mixture or individually:

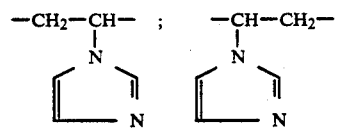

The compound of formula (II) thus obtained is then quaternized by alkylation with a compound of the formula RX, in which R and X have the meanings indicated above.

In the case where w=1 or 2, the products thus obtained are oxidized with hydrogen peroxide using a known process, at a temperature of between 20° and 50° C.

The process for the preparation of the compounds of the invention may be represented by the following reaction scheme:

SCHEME A

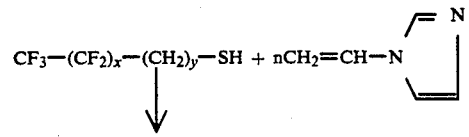

-continued
SCHEME A

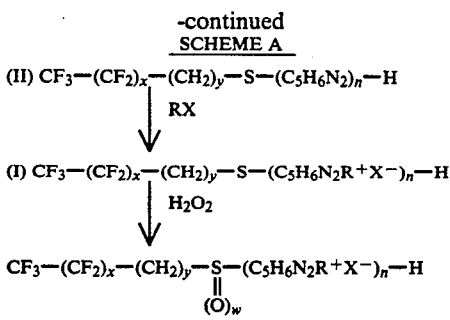

(II) $CF_3-(CF_2)_x-(CH_2)_y-S-(C_5H_6N_2)_n-H$ $\downarrow RX$ (I) $CF_3-(CF_2)_x-(CH_2)_y-S-(C_5H_6N_2R^+X^-)_n-H$ $\downarrow H_2O_2$ $CF_3-(CF_2)_x-(CH_2)_y-\underset{\underset{(O)_w}{\|}}{S}-(C_5H_6N_2R^+X^-)_n-H$ The radical reaction takes place in a solvent medium in the presence of a free radical initiator.

Free radical initiators which may be mentioned are hydroperoxides, such as tert-butyl hydroperoxide, peroxides, such as dibenzoyl peroxide, peresters, such as tert-butyl peroxybenzoate, or azo derivatives and in particular azobisisobutyronitrile.

The solvents which may be used must be inert with respect to the reagents and may be chosen from $C_1-C_4$ alcohols, such as methanol or isopropanol, alkyl ethers, glycol ethers, cyclic ethers, such as tetrahydrofuran, or $C_6-C_8$ aliphatic or aromatic hydrocarbons, such as toluene.

The starting mercaptan is dissolved in the solvent in the presence of 1-vinylimidazole and the free radical initiator is then added, the reaction being carried out under an inert atmosphere. The compounds of formula (II) thus obtained are then alkylated using an alkylating agent RX in the presence of an inert solvent, such as those mentioned above.

The alkylating agents RX used according to the invention are chosen, for example, from methyl halides, ethyl halides, methyl sulfates, ethyl sulfates, methylsulfonate, methyl para-toluenesulfonate or bromoethanol.

The compounds of formula (II) are novel and are another subject of the invention.

The cationic polyfluoroalkylthiopoly-(ethylimidazolium) compounds of formula (I) of the invention have good biocidal properties.

A good biocidal activity of these compounds has been observed using conventional methods on the following strains: *Pseudomonas aeruginosa, Staphylococcus aureus* and *Candida albicans*. These strains may be regarded as representing the main bacteria and fungi responsible for cutaneous disorders of bacterial or mycobacterial origin or disorders due to the implantation of pathogenic yeasts.

The low toxicity of the compounds of the invention has been observed by hemolysis of the erythrocytes from blood samples.

The compounds according to the present invention may be used as biocidal agents or as preservatives in the chemical industry sector, in particular in cosmetic products, and the pharmaceutical industry for human or veterinary use, in agricultural products, products for plant treatment, paints and varnishes and papermaking.

The compounds of the invention have valuable surfactant properties. Moreover, they have the characteristic of attaching themselves to keratinous materials, such as the skin, the hair and the nails.

Their cationic amphophilic character additionally imparts to them disentangling, softness, sheen and suppleness characteristics with respect to hair and softness characteristics with respect to the skin.

On the other hand, the presence of a perfluorinated chain in their structure makes it possible to impart a hydrophobic character and an oleophobic character to the treated skin or hair.

The compounds according to the invention permit rapid drying of the hair or prevent excessive regreasing of the skin and the hair.

The compounds of the invention are therefore particularly valuable for cosmetic care of keratinous materials. They are also particularly valuable for the treatment of cutaneous disorders of bacterial or mycobacterial origin or disorders due to the implantation of pathogenic yeasts. They may, in particular, be used in pharmaceutical compositions which are able to be applied topically to the skin or to the mucosa, for the treatment of acne or of mycoses, or in cosmetic compositions, in particular body deodorants or mouthwashes.

The invention therefore also relates to pharmaceutical or cosmetic compositions for the treatment or the care of human keratinous materials, said compositions containing, in a physiologically acceptable medium, an effective amount of compounds of formula (I) as defined above.

The compounds of formula (I) are present in concentrations of preferably between 0.1 and 10% by weight, with respect to the total weight of the composition, and preferably between 0.2 and 5% by weight.

These compositions may be aqueous, alcoholic or aqueous-alcoholic solutions, or emulsions in the form of a milk or cream, foam, gel, paste or stick or in the form of a spray.

These compositions may be pressurized in aerosol devices in the presence of a propellant, optionally in the presence of foam generators or emulsifiers.

Propellants which may be mentioned are agents of the freon type, $C_3-C_5$ alkanes, chlorinated solvents, such as methylene chloride, or ethers, such as dimethyl ether.

The compositions may also be in the form of a vesicular dispersion based on ionic lipids (liposomes) or nonionic lipids.

These compositions contain water, a physiologically acceptable solvent or a mixture of water and said solvent, the solvent being chosen from $C_1-C_4$ lower alcohols, such as ethanol, isopropanol or propanol, or polyalcohols, such as polyethylene glycol or glycerin, these solvents being present in proportions of between 0 and 50%.

The compositions according to the invention may also contain oils, natural or synthetic waxes, fatty alcohols, silicones, nonionic, cationic, weakly anionic, amphoteric or zwitterionic surfactants, foaming agents, emulsifiers or dispersants, polymers of natural origin, such as cellulose, guar or chitosan derivatives, peptides, synthetic polymers, conditioners, foam stabilizers, thickeners, agents for imparting a sheen, sterols, salts, sunscreens, perfumes, coloring agents, moisturizers and preservatives other than those of formula (I), in particular those of the isothiazolone family, such as 2-methylisothiazolone, 2-octylisothiazolone, 5-chloro-2-methylisothiazoline, benzoisothiazolone or those described in French Patent FR-2,492,376.

A particular form of cosmetic application according to the invention consists of compositions for washing and/or cosmetic treatment of hair with rinsing and rapid drying, said compositions containing at least one compound of formula (I) in the presence of detergents and foaming agents or conventional treatment agents compatible with the compounds of the invention.

These compositions may be in the form of a shampoo, an after-shampoo or a composition for rinsing the hair. They are applied in effective amounts for washing and/or treating the hair, then followed by rinsing with water.

The invention also relates to compositions for treatment of the skin, containing at least one compound of formula (I) in the presence of conventional treatment agents compatible with the compounds of the invention, so as to prevent excessive regreasing of the skin after application.

Another embodiment of the invention also consists of hair compositions in the form of a shampoo or lotion for the elimination of dandruff.

Another subject of the invention comprises a process for the cosmetic treatment of hair for the elimination of dandruff, using the composition.

The invention also relates to the use of the compounds of formula (I) for the preparation of a medicament for the treatment of cutaneous disorders of bacterial or mycobacterial origin or disorders due to implantations of pathogenic yeasts.

The examples which follow serve to illustrate the invention, without, however, any limitation being implied.

PREPARATION EXAMPLES

EXAMPLE 1

Preparation of a compound of formula (I) in which:
$x=5$ $y=2$ $n=1$ $R=CH_3$ $X=CH_3OSO_3^{\ominus}$

STEP 1

Preparation of a compound of formula (II) in which: $x=5$ $y=2$ $n=1$ 76 g of 2-F-hexylethanethiol (0.2 mol) in solution in 80 g of methanol are placed in a reactor. The mixture is stirred under a nitrogen atmosphere. 18.8 g of 1-vinylimidazole are then added in the course of 5 minutes. Heating is then started. When the temperature of the reaction mixture reaches 55° C., a solution of 0.752 g of azobisisobutyronitrile in 40 g of methanol is then added dropwise in the course of 1 h 30 while continuing to raise the temperature. When the addition is complete, the temperature of the reaction mixture is close to 66° C. The methanol refluxes.

Stirring, heating and the stream of nitrogen are maintained for 14 hours.

The reaction mixture then consists of monoaddition and diaddition products.

The monoaddition product is isolated by filtering through silica 60 H (eluent $CH_2Cl_2/CH_3OH:95/5$) with a yield of 80% (m=76 g).

Alkali number:2.07 meq/g (theoretical:2.10 meq/g)
Thioether index:2.05 meq/g (theoretical:2.10 meq/g)

| | ELEMENTAL ANALYSIS | |
|---|---|---|
| | THEORETICAL | FOUND |
| C | 32.92 | 32.69 |
| H | 2.34 | 2.45 |
| N | 5.91 | 5.84 |
| S | 6.76 | 7.10 |
| F | 52.08 | 51.84 |

STEP 2

Quaternization of the compound from Step 1.

23.7 g (0.05 mol) of the compound from Step 1 are dissolved in 25 ml of methanol in a reactor.

6.19 g of dimethyl sulfate are added dropwise at 25° in the course of 1 hour, whilst ensuring that the temperature of the reaction mixture does not rise above 35° C.

The mixture is stirred for 14 hours at ambient temperature. The solvent is then evaporated under reduced pressure. 30.70 g of a light brown paste are obtained.

| | ELEMENTAL ANALYSIS | |
|---|---|---|
| | THEORETICAL | FOUND |
| C | 30.01 | 29.74 |
| H | 2.85 | 3.05 |
| N | 4.67 | 4.41 |
| S | 10.68 | 10.34 |
| F | 41.14 | 40.83 |

EXAMPLE 2

Compound of Formula (I) in which: $x=5$ $y=2$ $n=2$
$X=CH_3OSO_3^{\ominus}$

STEP 1

Compound of formula (II) in which: $x=5$ $y=2$ $n=2$

This compound is prepared using the method of Example 1, Step 1.

The dicondensation product is isolated from the reaction mixture by filtering through silica 60 H (eluent $CH_2Cl_2/CH_3OH:95/5$).

In parallel to 76 g of 2-(2'-F-hexylethylthio)ethylimidazole (Example 1), 5 g of dicondensation product, 2-[2'-(2''-(2-F-hexylethylthio)ethylimidazole]-ethylimidazole, are obtained.

The product is in the form of a light brown paste.
Alkali number:3.45 meq/g (theoretical:3.52 meq/g)
Thioether index:1.70 meq/g (theoretical:1.76 meq/g)

| | ELEMENTAL ANALYSIS | |
|---|---|---|
| | THEORETICAL | FOUND |
| C | 38.03 | 37.16 |
| H | 3.01 | 3.25 |
| N | 9.86 | 9.58 |
| S | 5.64 | 5.56 |
| F | 43.45 | 41.30 |

STEP 2

Quaternization of the compound from Step 1

The method is analogous to that of Example 1, Step 2, using:

3.15 g of the compound from Step 1 dissolved in 5 g of methanol;

1.37 g of dimethyl sulfate.

4.5 g of quaternized product are obtained, which product is in the form of a beige paste.

| | ELEMENTAL ANALYSIS | |
|---|---|---|
| | THEORETICAL | FOUND |
| C | 32.20 | 31.48 |
| H | 3.56 | 3.78 |
| N | 6.83 | 6.50 |
| S | 11.72 | 10.90 |
| F | 30.10 | 31.86 |

EXAMPLE 3

Preparation of a Compound of Formula (I) in which:
x=5 y=2 n̄=3 R=CH₃ X=CH₃OSO₃⊖

STEP 1

Preparation of a compound of formula (II) in which:
x=5 y=2 n̄=3

The method is analogous to that of Example 1, Step 1, using:
- 38 g of 2-F-hexylethanethiol (0.1 mol) dissolved in 40 g of methanol;
- 29.61 g (0.3 mol) of 1-vinylimidazole;
- 1.12 g of azobisisobutyronitrile in 40 g of methanol.

After reaction, the solvent is evaporated under reduced pressure and 67.5 g of a light beige paste are obtained.

Alkali number:4.47 meq/g (theoretical:4.53 meq/g)
Thioethane index:1.60 meq/g (theoretical:1.51 meq/g)

STEP 2

Quaternization of the compound from Step 1
The method is analogous to that of Example 1, Step 2, using:
- 20 g of the compound from Step 1 dissolved in 50 ml of methanol;
- 11.26 g of dimethyl sulfate.

| ELEMENTAL ANALYSIS | | |
|---|---|---|
| | THEORETICAL | FOUND |
| C | 33.61 | 33.34 |
| H | 4.02 | 4.49 |
| N | 8.22 | 8.36 |
| S | 12.39 | 12.15 |
| F | 23.00 | 21.55 |

EXAMPLE 4

Preparation of a Compound of Formula (II) in which:
x=7 y=2 n=1 R=CH₃ X=CH₃OSO₃⊖

STEP 1

Preparation of a compound of formula (II) in which:
x=7 y=2 n=1

The method is analogous to that of Example 1, Step 1, using:
- 96 g of 2-F-octylethanethiol (0.2 mol) dissolved in 80 g of methanol;
- 18.8 g of 1-vinylimidazole (0.2 mol);
- 0.752 g of azobisisobutyronitrile in 40 g of methanol.

The reaction mixture consists of monoaddition and diaddition products.

The monoaddition product, 2-(2'-F-octylethylthio)ethylimidazole is isolated by filtration through Merck 60 H silica under the same conditions as for Example 1, Step 1.

Yield=85% (m=98 g)
Alkali number:1.69 meq/g (theoretical:1.74 meq/g)
Thioether index:1.75 meq/g (theoretical 1.74 meq/g)

| ELEMENTAL ANALYSIS | | |
|---|---|---|
| | THEORETICAL | FOUND |
| C | 31.36 | 31.09 |
| H | 1.92 | 1.90 |
| N | 4.88 | 4.89 |
| S | 5.57 | 5.45 |
| F | 56.27 | 55.86 |

STEP 2

Quaternization of the compound from Step 1.
The method is analogous to that of Example 1, Step 2, using:
- 43.05 g (0.075 mol) of the compound from Step 1 dissolved in 40 ml of methanol;
- 9.45 g of dimethyl sulfate.

52.50 g of a light chestnut paste are obtained.

| ELEMENTAL ANALYSIS | | |
|---|---|---|
| | THEORETICAL | FOUND |
| C | 29.14 | 28.89 |
| H | 2.43 | 2.59 |
| N | 4.00 | 3.74 |
| S | 9.14 | 9.11 |
| F | 46.14 | 45.84 |

EXAMPLE 5

Preparation of a Compound of Formula (I) in which:
x=7 y=2 n̄=1.5 R=CH₃ X=CH₃OSO₃⊖

STEP 1

Preparation of a compound of formula (II) in which:
x=7 y=2 n̄=1.5

The method is analogous to that of Example 1, Step 1, using:
- 96 g of 2-F-octylethanethiol (0.2 mol) dissolved in 80 g of methanol;
- 28.2 g (0.3 mol) of 1-vinylimidazole;
- 1.15 g of azobisisobutyronitrile in 40 g of methanol.

124 g of a beige-colored pasty product are obtained.
Alkali number:2.41 meq/g (theoretical:2.41 meq/g)
Thioether index:1.60 meq/g (theoretical:1.61 meq/g)

| ELEMENTAL ANALYSIS | | |
|---|---|---|
| | THEORETICAL | FOUND |
| C | 33.83 | 33.69 |
| H | 2.27 | 2.40 |
| N | 6.76 | 6.81 |
| S | 5.16 | 4.95 |
| F | 41.98 | 42.08 |

STEP 2

Quaternization of the compound from Step 1.
The method is analogous to that of Example 1, Step 2, using:
- 30 g of the compound from Step 1, dissolved in 37 ml of methanol;
- 9.11 g of dimethyl sulfate.

39 g of a light beige-colored pasty product are obtained.
Alkali number:0.1 meq/g.

| ELEMENTAL ANALYSIS | | |
|---|---|---|
| | THEORETICAL | FOUND |
| C | 30.38 | 30.31 |
| H | 2.86 | 2.86 |
| N | 5.18 | 5.06 |
| S | 9.89 | 10.09 |
| F | 39.95 | 39.55 |

EXAMPLE 6

Preparation of a Compound of Formula (II) in which:
 $x=7\ y=2\ \bar{n}=3\ R=CH_3\ X=CH_3OSO_3^{\ominus}$

STEP 1

Preparation of a compound of formula (II) in which:
$x=7\ y=2\ \bar{n}=3$

The method is analogous to that of Example 1, Step 1, using:
- 96 g (0.2 mol) of 2-F-octylethanethiol dissolved in 76 g of isopropanol;
- 56.4 g (0.6 mol) of 1-vinylimidazole;
- 2.24 g of azobisisobutyronitrile in 150 g of isopropanol.

Alkali number: 3.83 meq/g (theoretical: 3.93 meq/g)
Thioether index: 1.34 meq/g (theoretical: 1.31 meq/g)

| ELEMENTAL ANALYSIS | THEORETICAL | FOUND |
|---|---|---|
| C | 39.59 | 39.34 |
| H | 2.72 | 3.18 |
| N | 10.31 | 10.74 |
| S | 3.92 | 4.30 |
| F | 39.46 | 40.87 |

STEP 2

Quaternization of the compound from Step 1.
The method is analogous to that of Example 1, Step 2, using:
- 40 g of the compound from Step 1, dissolved in 30 ml of methanol;
- 19.3 g of dimethyl sulfate.

59.3 g of light beige product are obtained.

| ELEMENTAL ANNLYSIS | THEORETICAL | FOUND |
|---|---|---|
| C | 32.63 | 32.42 |
| H | 3.62 | 3.76 |
| N | 7.37 | 7.21 |
| S | 11.24 | 10.99 |
| F | 28.31 | 28.58 |

EXAMPLE 7

Preparation of a Compound of Formula (I) in which:
 $x=7\ y=2\ \bar{n}=5\ X=CH_3OSO_3^{\ominus}\ R=CH_3$

STEP 1

Preparation of a compound of formula (II) in which:
$x=7\ y=2\ \bar{n}=5$

The method is analogous to that of Example 1, Step 1, using:
- 48 g of 2-F-octylethanethiol (0.1 mol) dissolved in 85 ml of methanol;
- 47 g (0.5 mol) of 1-vinylimidazole;
- 1.88 g of azobisisobutyronitrile in 60 ml of methanol.

103.2 g of a beige colored product are obtained.
Alkali number: 4.62 meq/g (theoretical: 5.26 meq/g)
Thioether index: 1.11 meq/g (theoretical: 1.05 meq/g)

| ELEMENTAL ANALYSIS | THEORETICAL | FOUND |
|---|---|---|
| C | 44.21 | 44.56 |
| H | 3.71 | 4.74 |
| N | 14.73 | 14.96 |
| S | 3.37 | 4.04 |
| F | 33.97 | 32.01 |

STEP 2

Quaternization of the compound from Step 1.
The method is analogous to that of Example 1, Step 2, using:
- 30 g of the compound from Step 1, dissolved in 100 ml of methanol;
- 17.47 g of dimethyl sulfate.

47.5 g of light beige product are obtained.

EXAMPLE 8

Preparation of a Compound of Formula (I) in which:
 $x=7\ y=2\ n=2\ X=CH_3OSO_3^{\ominus}\ R=CH_3$

STEP 1

Preparation of a compound of formula (II) in which:
$x=7\ y=2\ n=2$

The method is analogous to that of Example 4, Step 1.
The dicondensation product is isolated from the reaction mixture by filtration through silica 60 H (eluent $CH_2Cl_2/CH_3OH$:95/5).

In parallel to the 98 g of 2-(2'-F-octylethylthio)ethylimidazole (Example 4), 7 g of dicondensation product, 2-[2'-F-octylethylthio)ethylimidazole]ethylimidazole, are obtained.

The product is in the form of a deep brown paste.
Alkali number: 2.79 meq/g (theoretical: 2.99 meq/g)
Thioether index: 1.37 meq/g (theoretical: 1.49 meq/g)

| ELEMENTAL ANALYSIS | THEORETICAL | FOUND |
|---|---|---|
| C | 35.95 | 35.14 |
| H | 2.50 | 2.70 |
| N | 8.38 | 7.89 |
| S | 4.79 | 4.72 |
| F | 48.35 | 47.54 |

STEP 2

Quaternization of the compound from Step 1.
The method is analogous to that of Example 1, Step 2, using:
- 6.5 g of the compound from Step 1, dissolved in 10 g of methanol;
- 2.22 g of dimethyl sulfate.

8.7 g of quaternized product are obtained, which product is in the form of a deep beige paste.

| ELEMENTAL ANALYSIS | THEORETICAL | FOUND |
|---|---|---|
| C | 31.30 | 30.59 |
| H | 3.15 | 3.43 |
| N | 6.09 | 5.78 |
| S | 10.43 | 10.04 |
| F | 35.15 | 33.91 |

EXAMPLE 9

Preparation of a Compound of Formula (I) in which:
x=7 y=2 n̄=10 X=CH$_3$OSO$_3$⊖ R=CH$_3$

STEP 1

Preparation of a compound of formula (II) in which:
x=7 y=2 n̄=10

The method is analogous to that of Example 1, Step 1, using:
- 20 g of 2-F-octylethanethiol (0.0417 mol) dissolved in 100 ml of methanol;
- 39.17 g of 1-vinylimidazole;
- 1.57 g of azobisisobutyronitrile.

After reaction, the solvent is evaporated under reduced pressure and 59 g of a light beige paste are obtained.

Alkali number: 6.08 meq/g (theoretical: 7.04 meq/g)

| | ELEMENTAL ANALYSIS | |
|---|---|---|
| | THEORETICAL | FOUND |
| C | 50.70 | 48.22 |
| H | 4.61 | 5.37 |
| N | 19.71 | 18.55 |
| S | 2.26 | 2.02 |
| F | 22.72 | 22.88 |

STEP 2

Quaternization of the compound from Step 1.

The method is analogous to that of Example 1, Step 2, using:
- 20 g of the compound from Step 1, dissolved in 60 ml of methanol;
- 15.32 g of dimethyl sulfate.

34.5 g of product are obtained.

| | ELEMENTAL ANALYSIS | |
|---|---|---|
| | THEORETICAL | FOUND |
| C | 35.82 | 34.25 |
| H | 4.70 | 5.29 |
| N | 10.44 | 10.05 |
| S | 13.15 | 11.80 |
| F | 12.04 | 11.99 |

EXAMPLE 10

Preparation of a Compound of Formula (I) in which:
x=5, y=2, n=1, R=benzyl, X=Cl⁻

100 g (0.211 mol) of the compound obtained in Step 1 of Example 1 are dissolved in 270 ml of dimethylacetamide in a 500 ml reactor. 26.7 g of benzyl chloride are added dropwise in the course of 5 minutes.

The mixture is heated at 70° C. for 20 hours.

After returning to ambient temperature, the solution is added dropwise in the course of 10 minutes to 800 ml of tetrahydrofuran. A pale yellow precipitate is obtained, which is filtered off and washed with twice 300 ml of tetrahydrofuran heated to 60° C.

After drying under vacuum in an oven, 88 g (70%) of a white solid are obtained, the $^{13}$C NMR spectrum of which is consistent with the expected structure.

The melting point of the N-(3-thio-5-F-hexyl)pentyl-benzylimidazolium chloride is 124° C.

| | ELEMENTAL ANALYSIS | |
|---|---|---|
| | THEORETICAL | FOUND |
| C | 39.98 | 39.87 |
| H | 3.02 | 3.07 |
| N | 4.66 | 4.62 |
| S | 5.34 | 5.32 |
| Cl | 5.90 | 5.88 |
| F | 41.10 | 41.05 |

EXAMPLE 11

Preparation of a Compound of Formula (I) in which:
x=5, y=2, n=1, R=C$_2$H$_5$, X=Br⁻

40 g (0.84 mol) of the compound obtained in Step 1, Example 1 are dissolved in 160 ml of tetrahydrofuran in a 500 ml reactor. When the reagent has dissolved completely, 18.4 g (0.168 mol) of ethyl bromide are added in the course of 5 minutes. This mixture is then heated for 36 hours with the solvent under reflux.

Heating is then stopped. When the temperature of the mixture has returned to 25° C., the presence of two phases is observed.

The upper phase is removed by decanting off. After three successive washes with 100 ml of tetrahydrofuran followed by removal of the solvent by decanting off and then drying of the residue under vacuum in an oven, 32 g (70%) of a water-soluble orange-colored paste are obtained, the $^{13}$C NMR spectrum of which is consistent with the expected structure.

| | ELEMENTAL ANALYSIS | |
|---|---|---|
| | THEORETICAL | FOUND |
| C | 30.89 | 30.05 |
| H | 2.77 | 2.81 |
| N | 4.80 | 4.73 |
| S | 5.50 | 5.68 |
| Br | 13.70 | 13.37 |
| F | 42.35 | 40.65 |

EXAMPLE 12

Preparation of a Compound of Formula (I) in which:
x=5, y=2, n̄=3, R=benzyl, X=Cl⁻

40 g of the random compound obtained in Step 1 of Example 3 are dissolved in 200 ml of dimethylacetamide at 80° C.

When all of the product has dissolved, 61.3 g of benzyl chloride are added in the course of 15 minutes at 80° C. The mixture is then heated at 80° C. for 24 hours and then brought to 25° C., at which temperature the product is precipitated, with stirring, by dropwise addition to 900 ml of tetrahydrofuran.

The product is then filtered off, washed with tetrahydrofuran (twice 300 ml) and then dried.

The precipitate, which is hygroscopic, is taken up in 600 ml of water. After it has been chilled in an ethanol+solid carbon dioxide bath, the solution is then lyophilized.

After this operation 44 g of a dry beige powder are obtained.

| | ELEMENTAL ANALYSIS | |
|---|---|---|
| | THEORETICAL | FOUND |
| C | 50.70 | 49.40 |
| H | 4.26 | 4.98 |
| N | 8.06 | 8.35 |

-continued

| ELEMENTAL ANALYSIS | | |
|---|---|---|
| | THEORETICAL | FOUND |
| S | 3.08 | 1.90 |
| Cl | 10.21 | 10.21 |
| F | 23.70 | 21.87 |

EXAMPLE 13

Preparation of a Compound of Formula (I) in which:
$x=5$, $y=2$, $n=1$, $R=CH_3$, $X=Cl^-$ 200 g of the compound obtained in Step 1 of Example 1, dissolved in 500 ml of dimethylacetamide, are introduced into a 1500 ml reactor. The reactor is then hermetically sealed and the solution is then heated to 75° C., with stirring. When this temperature is reached, gaseous methyl chloride is introduced into the reactor until the pressure inside the system reaches 1500 mbar.

When this pressure is obtained, the methyl chloride feed is stopped until all of the gas introduced has been consumed (return to atmospheric pressure inside the reactor). When the system consumes no further methyl chloride, the installation is purged with nitrogen. After the temperature has returned to 25° C., the product is precipitated in 1.5 liters of ethyl acetate, with vigorous stirring.

After removal of the solvent by decanting off, the residue obtained is washed with three times 200 ml of ethyl acetate. After drying in an oven, 153 g (70%) of a beige paste are obtained, the $^{13}C$ NMR spectrum of which is consistent with the expected structure.

| ELEMENTAL ANALYSIS | | |
|---|---|---|
| | THEORETICAL | FOUND |
| C | 32.04 | 30.59 |
| H | 2.69 | 3.25 |
| N | 5.33 | 5.33 |
| S | 6.11 | 5.91 |
| Cl | 16.76 | 5.88 |
| F | 47.06 | 46.96 |

EXAMPLE 14

Preparation of a Compound of Formula (I) in which:
$x=5$, $y=2$, $n=1$, $R=$hydroxyethyl, $X=Br^-$ 47.4 g of the compound obtained from Step 1 of Example 1 are dissolved in 135 ml of dimethylacetamide in a 500 ml reactor. 50 g (0.4 ml) of bromoethanol are added dropwise in the course of 10 minutes.

The mixture is heated at 70° C. for 48 hours.

After the temperature has returned to 25° C., the solution is precipitated in 200 ml of ethyl acetate. A pasty beige precipitate is obtained. The supernatant phase is removed by decanting off and the residue is washed with twice 200 ml of ethyl acetate.

The product is reprecipitated from 100 ml of ethyl acetate at 70° C. After the temperature has returned to 25° C., the solvent is removed by decanting off.

After drying in an oven, 35 g (50%) of a beige pasty product are obtained. The product is purified by liquid phase chromatography on Merck 60 H silica (eluent $CH_2Cl_2/CH_3OH$:90/10)

The $^{13}C$ NMR spectrum is in accordance with the expected structure.

EXAMPLE A

| OIL-IN-WATER EMULSION | |
|---|---|
| Hydrogenated polyisobutene | 6.5 g |
| Octyl palmitate | 5.0 g |
| Cyclomethicone | 5.0 g |
| Cetyl alcohol | 4.0 g |
| Glycerol stearate | 3.0 g |
| Glyerol | 3.0 g |
| Oxyethylenated polyethylene glycol stearate containing 40 mol of ethylene oxide, sold under the name "MYRJ 52" name by ICI | 2.0 g |
| Myristyl myristate | 2.0 g |
| Sorbitan tristearate | 0.9 g |
| Dipotassium salt of ethylene-diaminetetraacetic acid | 0.05 g |
| Compound from Example 5 | 5.0 g |
| Preservative qs | |
| Water qs | 100.0 g |

EXAMPLE B

| OIL-IN-WATER EMULSION | |
|---|---|
| Hydrogenated polyisobutene | 6.5 g |
| Octyl palmitate | 5.0 g |
| Cyclomethicone | 5.0 g |
| Cetyl alcohol | 4.0 g |
| Glycerol stearate | 3.0 g |
| Glyerol | 3.0 g |
| Oxyethylenated polyethylene glycol stearate containing 40 mol of ethylene oxide, sold under the name "MYRJ 52" by ICI | 2.0 g |
| Myristyl myristate | 2.0 g |
| Sorbitan tristearate | 0.9 g |
| Dipotassium salt of ethylene-diaminetetraacetic acid | 0.05 g |
| Compound from Example 7 | 2.5 g |
| Preservative qs | |
| Water qs | 100.0 g |

EXAMPLE C

| WATER-IN-OIL EMULSION | |
|---|---|
| Vaseline | 14.2 g |
| Vaseline oil | 12.2 g |
| Hydrogenated lanolin | 6.3 g |
| Isopropyl palmitate | 4.5 g |
| Mixture of ketearyl octanoate and isopropyl myristate, marketed under the name "PCL Liquide huile 2/066210" by DRAGOCO | 2.85 g |
| Magnesium lanolate | 2.7 g |
| Octoxyglyceryl palmitate | 1.9 g |
| Palm oil | 0.5 g |
| 5-chloro-2-(2,4-dichlorophenoxy)-phenol, marketed under the name "TRICLOSAN" by CIBA-GEIGY | 0.5 g |
| Lanolin alcohol sold under the name "HARTOLAN" by CRODA | 0.43 g |
| Compound from Example 5 | 5.0 g |
| Perfume qs | |
| Preservative qs | |
| Water qs | 100.0 g |

EXAMPLE D

| WATER-IN-OIL EMULSION | |
|---|---|
| Vaseline | 14.2 g |
| Vaseline oil | 12.2 g |
| Hydrogenated lanolin | 6.3 g |
| Isopropyl palmitate | 4.5 g |
| Mixture of ketearyl octanoate and isopropyl myristate, marketed under the name "PCL Liquide huile 2/066210" by DRAGOCO | 2.85 g |
| Magnesium lanolate | 2.7 g |
| Octoxyglyceryl palmitate | 1.9 g |
| Palm oil | 0.5 g |
| 5-chloro-2-(2,4-dichlorophenoxy)- | 0.5 g |

EXAMPLE D-continued

WATER-IN-OIL EMULSION

| | |
|---|---|
| phenol, marketed under the name "TRICLOSAN" by CIBA-GEIGY | |
| Lanolin alcohol sold under the name "HARTOLAN" by CRODA | 0.43 g |
| Compound from Example 7 | 2.5 g |
| Perfume qs | |
| Preservative qs | |
| Water qs | 100.0 g |

EXAMPLE E

DEODORANT SPRAY

| | |
|---|---|
| Compound from Example 7 | 1.0 g |
| Water | 50.0 g |
| Perfume | 1.0 g |
| 95° ethyl alcohol qs | 100.0 g |

EXAMPLE F

AQUEOUS STICK DEODORANT

| | |
|---|---|
| Compound from Example 3 | 0.23 g |
| Sodium stearate | 7.5 g |
| Propylene glycol | 65.0 g |
| Perfume | 1.0 g |
| Water qs | 100.0 g |

EXAMPLE G

SHAMPOO

| | |
|---|---|
| Alkylpolyglycoside sold under the name "APG 300 CS" as a solution containing 50% of active substance (AS) | 15.0 g AS |
| Compound of Example 9 | 5.0 g |
| Water qs | 100.0 g |
| Spontaneous pH = 5 | |

EXAMPLE H

SHAMPOO

| | |
|---|---|
| Sodium laurylsarcosinate sold under the name "ORAMIX L30" by SEPPIC | 15.0 g |
| Cocobetaine sold under the name "DEHYTON AB30" by HENKEL | 3.75 g |
| Compound from Example 3 | 0.2 g |
| Water qs | 100.0 g |
| Spontaneous pH = 7.2 | |

EXAMPLE I

SHAMPOO

| | |
|---|---|
| Compound from Example 4 | 2 g |
| Alkylpolyglycoside sold under the name "APG 300" by HENKEL | 15.0 G AS |
| Disodium salt of ethylenediamine-tetraacetic acid | 0.5 g AS |
| Preservatives | 0.3 g |
| Perfume | 0.5 g |
| pH = 6 qs | |
| Purified water qs | 100.0 g |

The shampoo permits rapid drying of damp hair.

EXAMPLE J

AFTER-SHAMPOO RINSE

| | |
|---|---|
| Compound from Example 5 | 1.0 g |
| Mixture of cetyl stearyl alcohol and oxyethylenated cetyl stearyl alcohol containing 33 mol of ethylene oxide, sold under the | 3.0 g |

EXAMPLE J-continued

AFTER-SHAMPOO RINSE

| | |
|---|---|
| name "SINNOWAX AO" by HENKEL | |
| Dimethyldialkylammonium chloride | 2.3 g |
| Colorant | 0.017 g |
| Preservative | 0.04 g |
| pH = 3.5 qs | |
| Purified water qs | 100.0 g |

This after-shampoo rinse permits rapid drying of damp hair.

EXAMPLE K

OIL-IN-WATER EMULSION

| | |
|---|---|
| Hydrogenated polyisobutene | 6.5 g |
| Octyl palmitate | 5.0 g |
| Cyclomethicone | 5.0 g |
| Cetyl alcohol | 4.0 g |
| Glycerol stearate | 3.0 g |
| Glycerol | 3.0 g |
| Oxyethylenated polyethylene glycol stearate containing 40 mol of ethylene oxide, sold under the name "MYRJ 52" by ICI | 2.0 g |
| Myristyl myristate | 2.0 g |
| Sorbitan tristearate | 0.9 g |
| Dipotassium salt of ethylene-diaminetetraacetic acid | 0.09 g |
| Compound from Example 10 | 2.5 g |
| Preservative qs | |
| Water qs | 100.0 g |

The compound from Example 10 may be replaced by the compound from Example 12.

EXAMPLE L

WATER-IN-EMULSION

| | |
|---|---|
| Vaseline | 14.25 g |
| Vaseline oil | 12.20 g |
| Hydrogenated lanolin | 6.3 g |
| Isopropyl palmitate | 4.5 g |
| Mixture of ketearyl octanoate and isopropyl myristate, marketed under the name "PCL LIQUIDE HUILE 2/066210" by DRAGOCO | 2.85 g |
| Magnesium lanolate | 2.7 g |
| Octoxyglyceryl palmitate | 1.9 g |
| Palm oil | 0.5 g |
| 5-chloro-2-(2,4-dichlorophenoxy)-phenol, marketed under the name "TRICLOSAN" by CIBA-GEIGY | 0.5 g |
| Lanolin alcohol sold under the name "HARTOLAN" by CRODA | 0.43 g |
| Compound from Example 12 | 0.5 g |
| Perfume qs | |
| Preservative qs | |
| Water qs | 100.0 g |

The compound from Example 12 may be replaced by the compound from Example 10.

We claim:

1. A composition for the care or the treatment of human keratinous materials, in particular the hair, the skin, the nails or the mucosa, which contains, in a physiologically acceptable medium an effective amount of a compound of formula (I)

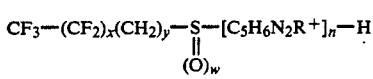

w is 0, 1 or 2;
x is between 2 and 10;
y is between 0 and 5;

R denotes a methyl, ethyl, hydroxyethyl or benzyl radical;

X⊖ denotes an inorganic or organic anion; and n is an integer or decimal number between 1 and 15; the group representing the following structures, taken as a mixture or individually:

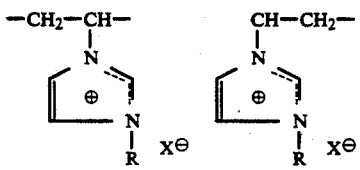

as a preservative or biocidal agent.

2. The composition as claimed in claim 1, which contains the compound of formula (I) in concentrations of between 0.1 and 10% by weight, with respect to the total weight of the composition.

3. The composition as claimed in claim 1, which is in the form of an aqueous, aqueous-alcoholic or alcoholic solution; an emulsion in the form of a milk or cream; a foam; a gel; a paste; a stick; a spray or vesicular dispersion or packaged as an aerosol.

4. The composition as claimed in claim 1, which contains water, a mixture of water and solvent(s) or a solvent, the solvent being physiologically acceptable and selected from the group consisting of $C_1$-$C_4$ monoalcohols and polyalcohols; the water, solvent or mixture thereof being present in proportions of between 0 and 50%.

5. The composition as claimed in claim 1, which also contains at least one additive selected from the group consisting of oils, fatty alcohols, silicones, natural or synthetic waxes, nonionic, cationic, weakly anionic, amphoteric or zwitterionic surfactants, polymers of natural or synthetic origin, conditioning agents, foam stabilizers, thickeners, agents for imparting a sheen, sterols, salts, sunscreens, preservatives other than those of formula (I), perfumes, colorants and moisturizers.

6. A pharmaceutical composition intended for topical application for the treatment of cutaneous diseases of bacterial or mycobacterial origin or due to implantations of pathogenic yeasts, comprising an effective amount of a compound of formula (I) as claimed in claim 1 as a preservative or biocidal agent.

* * * * *